US012674124B2

(12) United States Patent
Höhnel et al.

(10) Patent No.: US 12,674,124 B2
(45) Date of Patent: Jul. 7, 2026

(54) WELL FOR CULTIVATING BIOLOGICAL MATERIAL

(71) Applicant: Sun Bioscience SA, Lausanne (CH)

(72) Inventors: Sylke Höhnel, Lausanne (CH); Nathalie Brandenberg, Lausanne (CH)

(73) Assignee: Doppl SA, Lausanne (CH)

( * ) Notice: Subject to any disclaimer, the term of this patent is extended or adjusted under 35 U.S.C. 154(b) by 0 days.

(21) Appl. No.: 17/059,786

(22) PCT Filed: Feb. 27, 2019

(86) PCT No.: PCT/IB2019/051590
§ 371 (c)(1),
(2) Date: Nov. 30, 2020

(87) PCT Pub. No.: WO2019/229545
PCT Pub. Date: Dec. 5, 2019

(65) Prior Publication Data
US 2021/0301237 A1     Sep. 30, 2021

(30) Foreign Application Priority Data
May 30, 2018     (CH) .................................... 00688/18

(51) Int. Cl.
*C12M 1/32*     (2006.01)

(52) U.S. Cl.
CPC ................................... *C12M 23/12* (2013.01)

(58) Field of Classification Search
CPC . B01L 2300/0829; C12M 23/12; C12M 25/04
See application file for complete search history.

(56) References Cited

U.S. PATENT DOCUMENTS

| | | | |
|---|---|---|---|
| 2008/0085556 A1* | 4/2008 | Graefing ................ | C12M 23/12 435/303.1 |
| 2010/0221768 A1* | 9/2010 | Akai ...................... | C12M 23/10 435/29 |
| 2014/0156455 A1 | 6/2014 | Atwood et al. | |
| 2014/0322806 A1 | 10/2014 | Bennett et al. | |
| 2018/0187136 A1* | 7/2018 | Lichtenberg ........... | C12M 23/20 |
| 2018/0264465 A1 | 9/2018 | Hohnel et al. | |
| 2019/0100786 A1* | 4/2019 | Kwon ................... | G01N 33/50 |
| 2019/0144808 A1 | 5/2019 | Cao et al. | |
| 2020/0399571 A1* | 12/2020 | Deutsch ................ | C12M 23/12 |

FOREIGN PATENT DOCUMENTS

| | | |
|---|---|---|
| JP | 6278590 B2 | 2/2018 |
| WO | WO2014156455 A1 | 10/2014 |
| WO | WO2016103002 A1 | 6/2016 |
| WO | WO2017214117 A1 | 12/2017 |

OTHER PUBLICATIONS

International Search Report for International Application No. PCT/IB2019/051590 dated May 29, 2019 (4 pages).
Written Opinion for International Application No. PCT/IB2019/051590 dated May 29, 2019 (6 pages).

* cited by examiner

*Primary Examiner* — Duane Smith
*Assistant Examiner* — Austin Q Le
(74) *Attorney, Agent, or Firm* — Muncy, Geissler, Olds & Lowe, P.C.

(57)     ABSTRACT

In a well for cultivating biological material, the well includes a top opening and a bottom area. The bottom area includes a first internal edge.

13 Claims, 19 Drawing Sheets

B–B'

A – A'

B–B'

W

15

WELL FOR CULTIVATING BIOLOGICAL MATERIAL

TECHNICAL FIELD

The disclosure relates to a well for cultivating biological material, and relates to a multi-well plate.

BACKGROUND

Wells for cultivating biological material, in particular cells of living organisms, are widely used in laboratories. Such wells are typically integrated in multi-well plates, wherein each multi-well plate comprises a multitude of wells, typically arranged in a symmetrical pattern on the multi-well plate. One possibility to arrange wells on a multi-well plate is a 4×6 pattern, in which 24 wells are arranged in four lines and six columns such as to create a regular pattern of 24 wells on the culture plate. Other possibilities include 6×8 patterns, 8×12 patterns or yet 16×24 patterns.

It is furthermore known to put drops of hydrogel onto the bottoms of such wells. Such hydrogel drops can either already comprise the biological material to be cultivated, or such hydrogel drops can be used to form a particular geometrical pattern on the bottoms of the wells.

PCT/IB2014/067242 for example describes a microwell structure at the bottom of wells of a multi-well plate, wherein the microwell structure is obtained by stamping a negative or mold into a hydrogel drop at the bottom of a well, leading to a thin microstructured hydrogel coating attached to the bottom of a multi-well plate.

However, properly handling a hydrogel at a bottom of a well can be a tricky task.

For example, when placing a hydrogel drop comprising cells to be cultivated on a flat bottom of a well, it can happen that the drop slowly migrates or spreads towards a vertical side wall of the well where it then forms a concave meniscus. The formation of such a meniscus has a strongly disadvantageous influence on cell growth and makes it almost impossible to analyze the cell growth in the hydrogel, for example by means of microscopy.

Also when stamping a microwell-structure into a hydrogel drop on the bottom of a well, the formation of a concave meniscus at the vertical side wall of the well can be highly disadvantageous because it can cause bubbles under the mold and can therefore lead to inhomogeneous and malformed microwell structures.

SUMMARY

It is an object of the disclosure, per an embodiment, to solve or to at least diminish the above-mentioned disadvantages. In particular, it is an object of the disclosure, per an embodiment, to find a solution to make it easier to handle a hydrogel drop at the bottom of a well.

This problem is solved, per an embodiment, by a well for cultivating biological material, wherein the well comprises a top opening and a bottom area, wherein the bottom area comprises a first internal edge.

The inventors have found that such an internal edge in the bottom area of the well has a meniscus-modifying influence: the formation of a concave meniscus at the side wall of the well is avoided and in addition to that a convex meniscus or dome of the hydrogel can be created. The internal edge keeps the hydrogel from migrating towards a vertical side wall of the well, thereby avoiding the formation of a concave meniscus at this location and the above-mentioned negative effects.

In the context of this application, the expression"well" shall refer to an elongated hole, for example having the form of a hollow cylinder, which typically at least partly has a round section. However, an at least partly rectangular section and/or an at least partly elliptical section and/or an at least partly polygonal section is/are in principle also possible. Furthermore, a well according to the disclosure might—in certain embodiments—comprise two parallel hollow cylinders which run parallel and which at least partly overlap. The expression"biological material" relates to human cells or animal cells, for example stem cells. The expression "hydrogel" relates to networks of polymer chains that are hydrophilic and/or to hydrogels as described in the international patent application PCT/IB2014/067242, the entire content of which is hereby incorporated by reference into this application. The expression"bottom" is to be understood such that it refers to the lowest surface or point of a well, wherein the well is closed on the side of the bottom and open on a side opposite the bottom. Furthermore, "bottom" can mean a plastic bottom of a standard multi-well plate or an imaging-bottom (thin glass or polymer) attached to a bottom-less multi-well plate. When cells are being cultured in the well, these cells are typically arranged at the bottom or near the bottom. The"bottom area" is an area extending upwards from the bottom (i.e. towards the well's opening) for a predetermined distance, for example a distance of 1 to 8 mm, preferably 2 to 7 mm, more preferably 3 to 4 mm. In preferred embodiments, the first internal edge is a shoulder, preferably an essentially circumferential shoulder, which causes a diameter of the well to diminish towards the bottom. However, the first internal edge is not necessarily circumferential. It can also only run along a certain percentage of an inner wall of the well. In any case, the edge preferably runs along the inner wall of the well in an essentially horizontal direction.

In some embodiments, the well is configured to receive a hydrogel drop in its bottom area, wherein the first internal edge is configured to force the hydrogel to develop a dome surface after a hydrogel drop of sufficient volume has been placed in the bottom area of the well. A dome can also be described as convex meniscus. "Sufficient volume" shall be understood as a volume that is slightly larger than a volume of a hole created by the bottom of the well and the first internal edge, wherein the volume is not so large that spill-over onto the first internal edge is caused. Such a convex meniscus has for example the advantage to make a molding of the hydrogel, for example for creating a microwell-structure in the hydrogel, easier. In some embodiments, the first internal edge is configured to keep a hydrogel drop injected into the bottom area of the well from reaching a side wall of the well. In some embodiments, the volumes of the hydrogel drops are between 5 and 50 ml_ for well-plates with 96 wells and/or between 25 and 200 ml_ for well-plates with 24 wells and/or between 1 and 10 pL for well-plates with 384 wells and/or between up to 1 ml_ for well-plates with 6 or 12 wells.

In some embodiments, the well comprises a microwell-structure, wherein the microwell structure comprises a multitude of microwells, wherein the microwell-structure is formed in the hydrogel in the bottom area of the well. Such a microwell-structure, which is preferably, per an embodiment, a microwell-structure as disclosed in PCT/IB2014/067242 has the advantage of multiplying a number of cell colonies that can be colonized in a multi-well plate because one separate colony can be grown in each microwell. However, it is also possible to grow only one colony per well or to grow a non-microstructured hydrogel dome per well with cells dispersed through the hydrogel dome. In this case, a microwell structure inside the well is not necessary.

In some embodiments, the well comprises a second internal edge, wherein the first internal edge and/or the second internal edge are preferably, per an embodiment, at least partly essentially circumferential and/or at least partly essentially ring-like. A second internal edge has the advantage, per an embodiment, that it can be used to avoid the formation of a concave meniscus at another location of the well, i.e. a location of the well which is different than the location where the first internal edge is placed. Circumferential and ring-like internal edges have the advantage, per an embodiment, of providing good symmetry and of being very efficient. However, it could also be possible to use for example internal edges composed of several distinct sections. In some embodiments, the first edge and/or the second internal edge are annular, preferably circular structures, preferably circled around a longitudinal axis of the well and preferably running around an internal wall of the well. In some embodiments, at least one of the internal edges is an internal ring and/or is and/or is comprised in a circular shoulder. In some embodiments, the first internal edge is located between a bottom of the well and the second internal edge. In some embodiments, the well comprises an essentially flat bottom wherein the first internal edge is formed by a ring sitting on the flat bottom of the well. The ring forming the first internal edge typically has an internal diameter of 1 to 35 mm, preferably 3 to 20 mm, more preferably 5.4 to 9.5 mm. The ring forming the first internal edge typically has height of 0.1 to 0.8 mm, preferably 0.15 to 0.6 mm, more preferably 0.2 to 0.3 mm. In some embodiments, the second internal edge is formed by a ring, wherein this ring has an internal diameter of 1.5 to 35 mm, preferably 3 to 20 mm, more preferably 5.8 to 9.9 mm.

In some embodiments, the well is at least partly essentially cylindrical, wherein the well comprises an upper cylinder extending from the top opening to the second internal edge, wherein the bottom area typically extends from the second internal edge to the bottom of the well, wherein the upper cylinder and/or the bottom area are typically at least partly essentially cylindrical, typically cylindrical with an essentially round section. Such an arrangement has the advantage, per an embodiment, of being comparably easy to manufacture and of offering comparably good functionality. The upper cylinder and/or the bottom area are typically circular hollow cylinders, wherein in some embodiments, especially in case of the upper cylinder one or more pieces of the cylinder do not necessarily have to be present. In some embodiments, the upper cylinder has a height of 2.5 to 35 mm, preferably 4 to 25 mm, more preferably 6.35 to 15.6 mm. In some embodiments, the bottom area has a height of 1.0 to 8.0 mm, preferably 2. to 6 mm, more preferably 3.0 to 4.0 mm.

In some embodiments, an internal diameter of the bottom area is smaller than an internal diameter of the upper cylinder. In some embodiments, the well comprises a first hollow cylinder, wherein the first hollow cylinder comprises a first top rim, wherein at least a part of the first top rim forms the first internal edge, wherein the first hollow cylinder typically extends from the bottom of the well towards the top opening, wherein the first hollow cylinder is placed concentrically inside the bottom area wherein an external diameter of the first hollow cylinder typically equals the internal diameter of the bottom area. This has the advantage, per an embodiment, of representing a comparably straight-forward implementation. However, other implementations are also possible, for example a first internal edge in the form of lamellae.

In some embodiments, the well comprises a second hollow cylinder, wherein the second hollow cylinder comprises a second top rim, wherein at least a part of the second top rim forms the second internal edge. In some embodiments, the first top rim comprises an external rim section and an internal rim section, wherein the first internal edge is formed by the internal rim section, wherein the second hollow cylinder is arranged on top of the first hollow cylinder, in particular on top of the external rim section of the first hollow cylinder, wherein the first hollow cylinder and the second hollow cylinder are coaxial. This arrangement has the advantage, per an embodiment, of being comparably straight-forward and comparably easy to manufacture. However, other implementations are also possible, for example a second internal edge in the form of lamellae. In some embodiments, a wall thickness of the first cylinder is larger than a wall thickness of second cylinder. In particular the first cylinder preferably has a wall thickness of approximately 0.4 mm and the second cylinder preferably has a wall thickness of 0.5 to 0.7 mm. The inventors have found that such dimensions, per an embodiment, are particularly advantageous for avoiding the formation of menisci while leaving enough space for growing cell material.

In some embodiments, the upper cylinder and the bottom area and the first internal edge are molded into one and the same workpiece, wherein the second internal edge is typically also molded into the same workpiece, wherein the workpiece is typically made from plastic and/or wherein a wall thickness of the workpiece is typically essentially constant throughout the entire well. In this context, "essentially constant" is to be understood as meaning "deviations of up to +/−25% are tolerated". It is also possible to use 3D printing instead of or in combination with molding for creating the workpiece or at least parts of it.

In some embodiments, the well comprises a pipetting notch, wherein the pipetting notch is typically cylindrical, preferably essentially circular cylindrical, wherein a longitudinal axis of the pipetting notch and a longitudinal axis of the upper cylinder (which is preferably also the longitudinal axis of the bottom area) are typically parallel, wherein a distance between the longitudinal axis of the pipetting notch and the longitudinal axis of the upper cylinder is typically smaller than a sum of an inner radius of the upper cylinder and an inner radius of the pipetting notch, such that the upper cylinder and the pipetting notch overlap, at least along a fraction of the depth of the well, such that an opening is present between the pipetting notch and the upper cylinder. Such a pipetting notch has the advantage, per an embodiment, of allowing a topping-up of a culture medium in the well while limiting the disturbing effect of this topping-up on cell colonies already present in the bottom area of the well. In some embodiments, the upper cylinder and the pipetting notch are both partial hollow cylinders, the expression "partial hollow cylinder" meaning a hollow cylinder which does not have a fully circular section but a section that corresponds only to a fraction of a circle. In other embodiments, the pipetting notch is at least partly not cylindrical but at least partly takes any other shape, such as conical, with the cone tip extending towards the bottom, or rectangular.

In some embodiments, a height of the pipetting notch equals, at least approximately, the sum of a height of the upper cylinder and a height of the bottom area, wherein the well typically comprises a barrier wall located between the pipetting notch and the bottom area, wherein a height of the barrier wall typically equals, at least approximately, the height of the bottom area.

In some embodiments, the barrier wall is typically formed by the combination of the first internal edge and the second internal edge, wherein the first internal edge and the second internal edge are rings centered around a longitudinal axis of the bottom area which coincides with the longitudinal axis of the upper cylinder. This has the advantage, per an embodiment, of being a simple way of creating the barrier wall.

In some embodiments, the pipetting notch has a diameter between 2 and 6 mm, preferably between 3 and 6 mm, more preferably between 4 and 6 mm. In some embodiments, the upper cylinder has a diameter between 2.5 and 35 mm, preferably between 4 and 25 mm, more preferably between 6.35 and 15.6 mm. In some embodiments, the well has a depth between 6.5 and 30 mm, preferably between 8 and 25 mm, more preferably between 10.67 and 17.4 mm.

A multi-well plate according to the disclosure comprises a multitude of wells according to any of the embodiments of the disclosure.

In some embodiments, the multi-well plate comprises a main body, wherein the wells and/or all hollow cylinders and/or all internal edges and/or all pipetting notches are molded into the main body, wherein a wall thickness of the main body is typically essentially constant throughout the main body. In this context, "essentially constant" is to be understood as meaning "deviations of up to +/−25% are tolerated". For forming the multi-well plate, other manufacturing methods are also possible. For example, it seems also possible to modify plastic plates after they are molded, by 3D printing into an existing plastic plate without notches.

A method for manufacturing a multi-well plate according to emboidments of the disclosure, comprises the steps:

forming a main body comprising a multitude of wells according to any of the embodiments of the disclosure, wherein the main body is preferably formed by means of injection molding, injecting a hydrogel drop into the bottom area of each well, and stamping a microwell-structure into each hydrogel drop.

BRIEF DESCRIPTION OF THE FIGURES

In the following, the disclosure is described in detail by means of a drawing, wherein shows.

DETAILED DESCRIPTION

Figure 1:
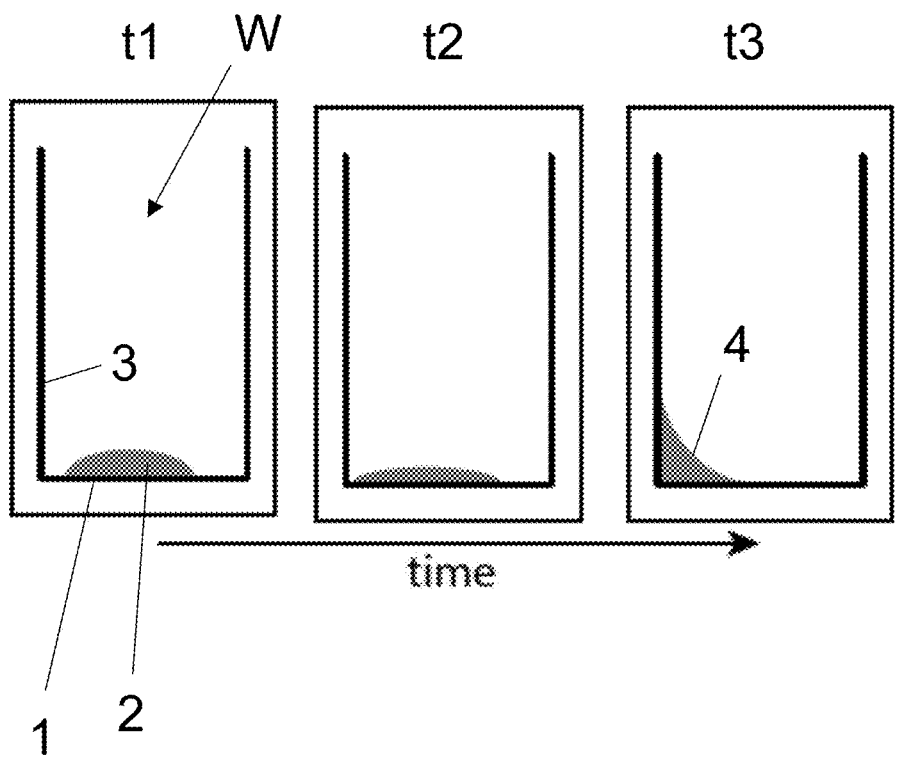
FIG. 1: A schematic visualization of a shortcoming of the prior art.

FIG. 1 shows a schematic visualization of a shortcoming of the prior art. In particular, a well W is shown at three different moments in time t1, t2, t3. The well W comprises a vertical side wall 3 and a flat bottom 1. The well W has the form of a cylindrical hole with a round cross section. This round cross section is not perceivable in FIG. 1 because this figure shows a longitudinal section through the well W. At moment t1, a hydrogel drop 2 is put on the bottom 1. This hydrogel drop has not been put directly in the center of the bottom 1 and slowly migrates towards the vertical side wall 3. At moment t2, the hydrogel drop has become flatter and has almost reached the vertical side wall 3. At moment t3, it has reached the vertical side wall 3 and has formed a meniscus 4. A formation of a meniscus 4 can also happen when the hydrogel drop 2 is placed in the center of the well W, when a spreading area of the hydrogel drop 2 is larger than the bottom surface of the well W.

Figure 2:
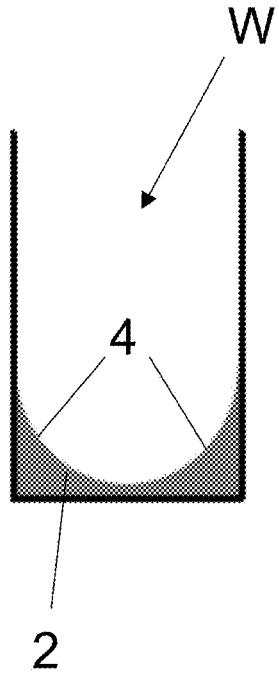
FIG. 2: A schematic visualization of another shortcoming of the prior art.

FIG. 2, which is a schematic visualization of another shortcoming of the prior art, shows a similar effect: a hydrogel drop 2 has been put into a well W (comparable to the one shown in FIG. 1), but the spreading area of the hydrogel drop 2 in FIG. 2 is larger than the bottom surface of the well W. Therefore, the meniscus 4 is formed all around the vertical side wall 3 of the well W.

As explained above, if the hydrogel drop 2 contains cells to be cultured, the formation of the meniscus 4 makes the distribution of the cells in the hydrogel drop 2 inhomogeneous and makes it difficult to examine the hydrogel, for example by means of microscopy.

Figure 3:
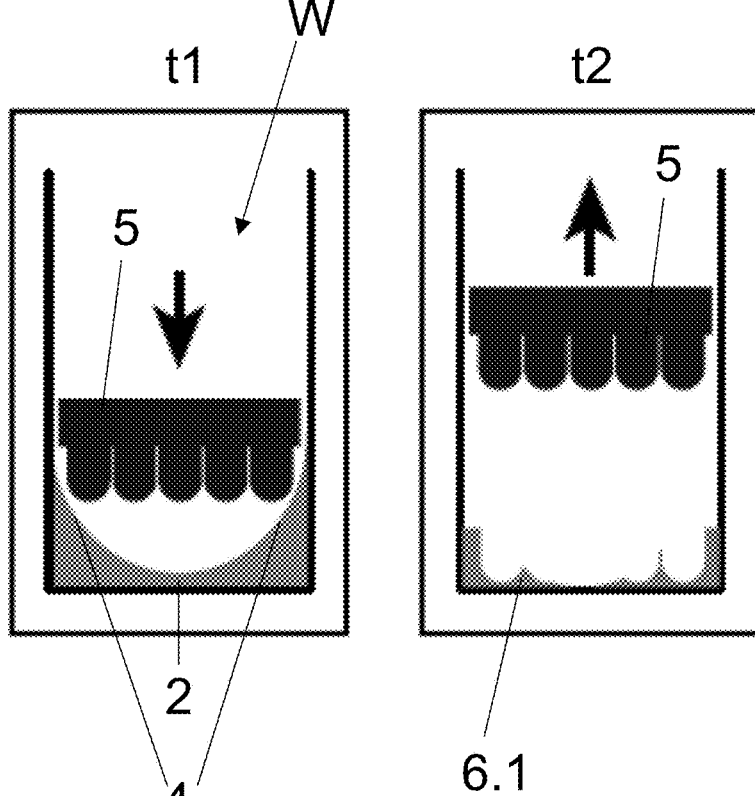
FIG. 3: A schematic visualization of another shortcoming of the prior art.

FIG. 3 shows a schematic visualization of another shortcoming of the prior art. In particular, FIG. 3 shows a well W comparable to the ones shown in FIGS. 1 and 2. The well W in FIG. 3 is shown at two different moments in time, namely t1 and t2. The well W also comprises a hydrogel drop 2 which has already formed a concave meniscus 4 (see moment t1). The purpose of the hydrogel in FIG. 3 is to serve as a material for a microwell-structure which is to be molded into the hydrogel by means of a stamp 5. At moment t1, the stamp 5 is lowered onto the hydrogel drop 2, which has formed a meniscus 4. At moment t2, the molding process is over and the stamp 5 is lifted. It can be observed that a malformed microwell-structure 6.1 has resulted from molding process. The reason for this is the fact that the hydrogel drop 2 had previously developed the concave meniscus 4 and air was trapped underneath the stamp.

Figure 4:
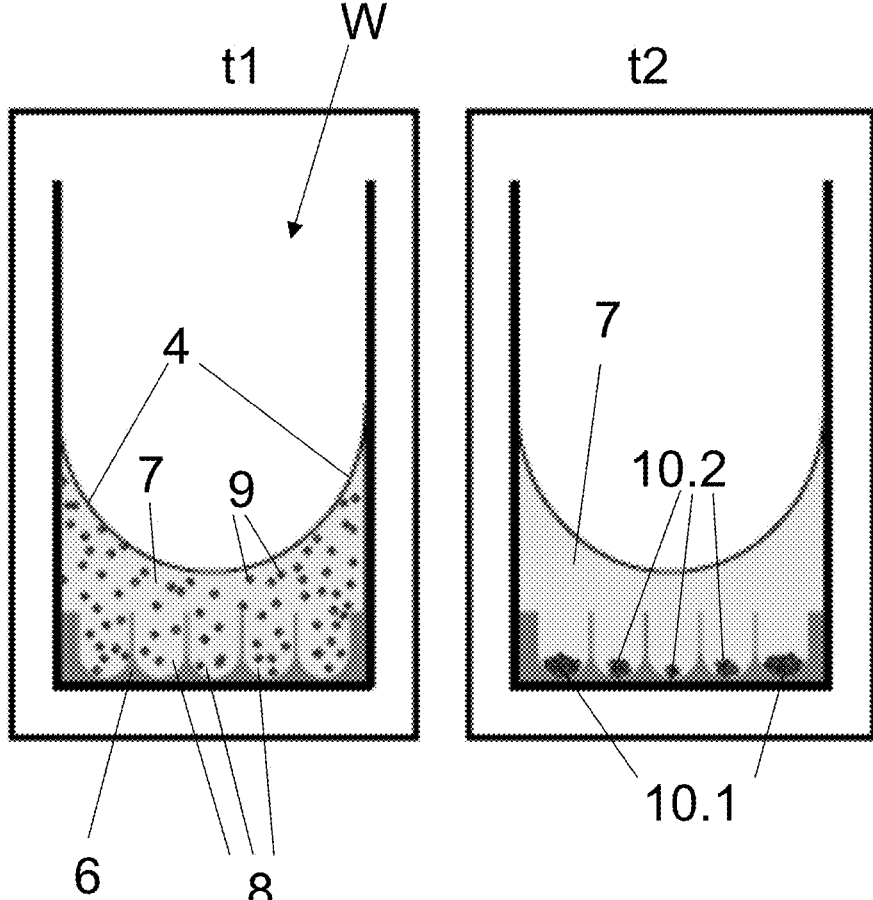
FIG. 4: A schematic visualization of another shortcoming of the prior art.

FIG. 4 shows a schematic visualization of another shortcoming of the prior art. In particular, FIG. 4 shows yet again a well W comparable to the ones shown in the previous Figures. Also in FIG. 4, the well W is shown at two moments in time, namely t1 and t2. The well comprises a microwell-structure 6 (which is properly and homogenously formed, in contrast to the malformed microwell-structure 6.1 shown in FIG. 3). The microwell-structure 6 comprises a plurality of microwells 8. The purpose of each microwell 8 is to grow a distinct cell colony. The well W is partly filled with a culture medium 7, which typically comprises a multitude of cells 9 in a nutrient solution. At moment t1, the culture medium 7 has just been filled into the well W. The cells 9 are floating around in the culture medium 7, and the culture medium 7 has developed a concave meniscus 4 all around the vertical side wall of the well W. At moment t2, some time has lapsed, and the cells have sedimented at the bottom of the well, namely in the different microwells 8.

However, due to the fact that the culture medium has developed a concave meniscus 4, more cells 9 have sedimented towards the exterior microwells 8 than have sedimented towards the interior microwells 8. Therefore, the cell colonies do not have equal sizes, but the cell colonies in exterior microwells are too large cell colonies 10.1 and the cell colonies in interior microwells are too small cell colonies 10.2.

FIGS. 1 to 4 make it clear that the formation of certain menisci in wells for cultivating biological material can be disadvantageous.

Figure 5:
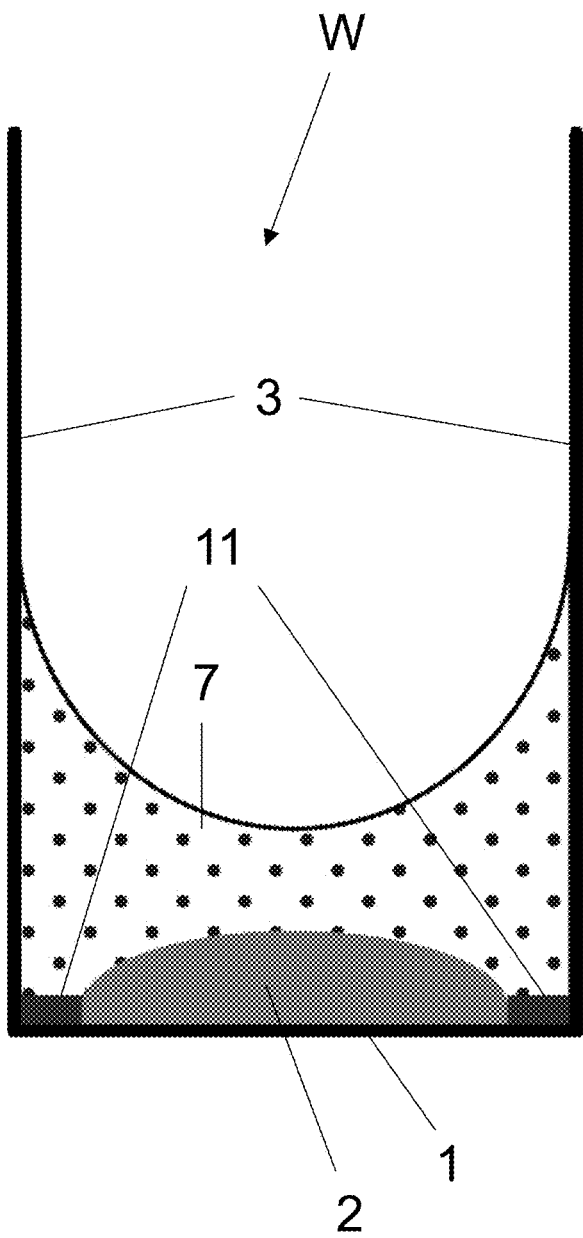
FIG. 5: A schematic visualization of a first embodiment of a well according to the disclosure (sectional view)

FIG. 5 is a schematic visualization of a first embodiment of a well W according to an embodiment of the disclosure, namely a longitudinal cut through a well W comparable to the wells W of the prior art shown in FIGS. 1 to 4. In particular, the Well W in FIG. 5 has the form of a cylindrical hole with a vertical side wall 3 which is tubular (since the well W has a round cross section—which is, however not perceivable in FIG. 5 because this figure shows a longitudinal cut through the well W). In contrast to the wells W of the prior art shown in FIGS. 1 to 4, well W in FIG. 5 comprises a first internal edge 11. The first internal edge 11 has the form of a ring with a rectangular cross section. The first internal edge 11 is located at the bottom 1 of the well W and is furthermore attached to the vertical side wall 3. Like this, the first internal edge 11, which sits in a circumferential manner at the bottom 1 of the well W, creates a flat hole at the bottom of the well W. FIG. 5 shows that the first internal edge 11 of the well W keeps a hydrogel drop 2 injected at the bottom of the well W from forming a meniscus with the vertical side wall 3 of the well W. The first internal edge 11 rather forces the hydrogel drop 2 to develop a convex dome instead of a concave meniscus. The well W shown in FIG. 5 is furthermore filled with a culture medium 7. It should be understood that the dots shown in this Figure (and in the following figures) do not necessarily correspond to cells. The dotted pattern has rather been chosen to represent the culture medium 7 as such, also when it actually only corresponds to a nutrient solution. The culture medium 7 forms a meniscus at the vertical side wall 3 of the well W.

Figure 6:
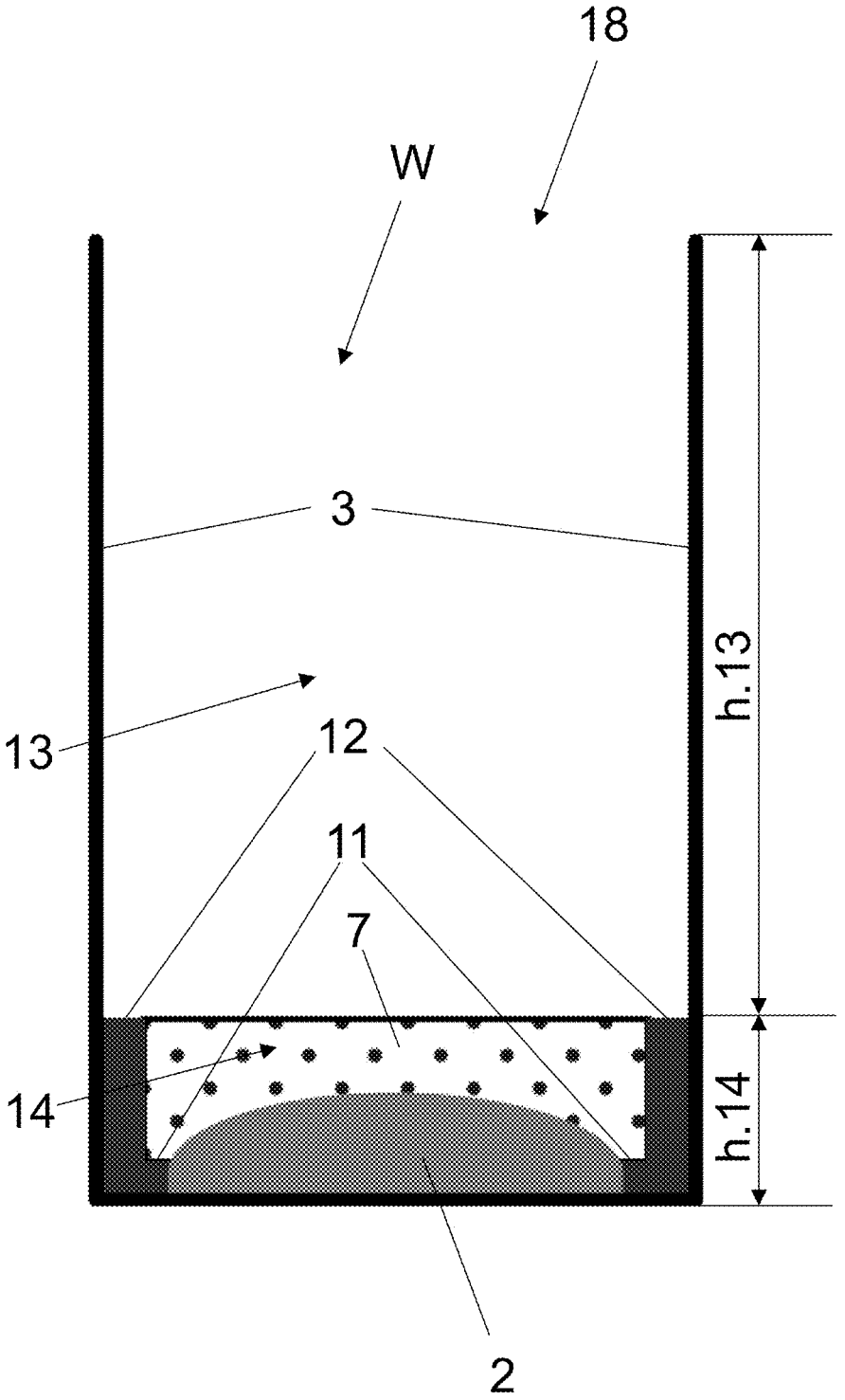
FIG. 6: A schematic visualization of another embodiment of a well according to the disclosure (sectional view)

FIG. 6 shows a schematic visualization of another embodiment of a well W according to the disclosure, yet again in a longitudinal cut view. The well W corresponds to the well W shown in FIG. 5, the sole difference being that the well W in FIG. 6 comprises a second internal edge 12 in addition to the first internal edge 11. The second internal edge 12 in FIG. 6 is also a ring with a rectangular section (like the first internal edge 11 described above for FIG. 5), but the second internal edge 12 has a larger internal diameter than the first internal edge 11 and is higher than the first internal edge 11 (wherein"higher" refers to the vertical direction in FIG. 6). The second internal edge 12 is placed on top of the first internal edge 11 (that is, on a side of the ring-shaped internal edge 11, which is opposite to the side with which the first internal edge 11 sits on the bottom of the well). This combination of two edges leads to a well W with the following advantages: not only the hydrogel drop 2 is kept from forming a concave meniscus with the vertical side wall 3 of the well W, but also a culture medium 7 is kept from forming such a meniscus. The advantages resulting from this are for example a quality increase in imaging by microscopy and a reduction of volume of culture medium or staining solutions required to cover the entire hydrogel dome. In FIG. 6 are furthermore indicated two different sections of the well W, namely an upper cylinder 13 and a bottom area 14, both of which share a common longitudinal axis. The bottom area 14 extends in vertical direction from the bottom of the well W to the height where the second internal edge terminates. The bottom area 14 has a height h.14. The upper cylinder 13 extends from the second internal edge 12 upwards until a top opening 18 of the well W. The upper cylinder 13 has a height h.13.

Figure 7:
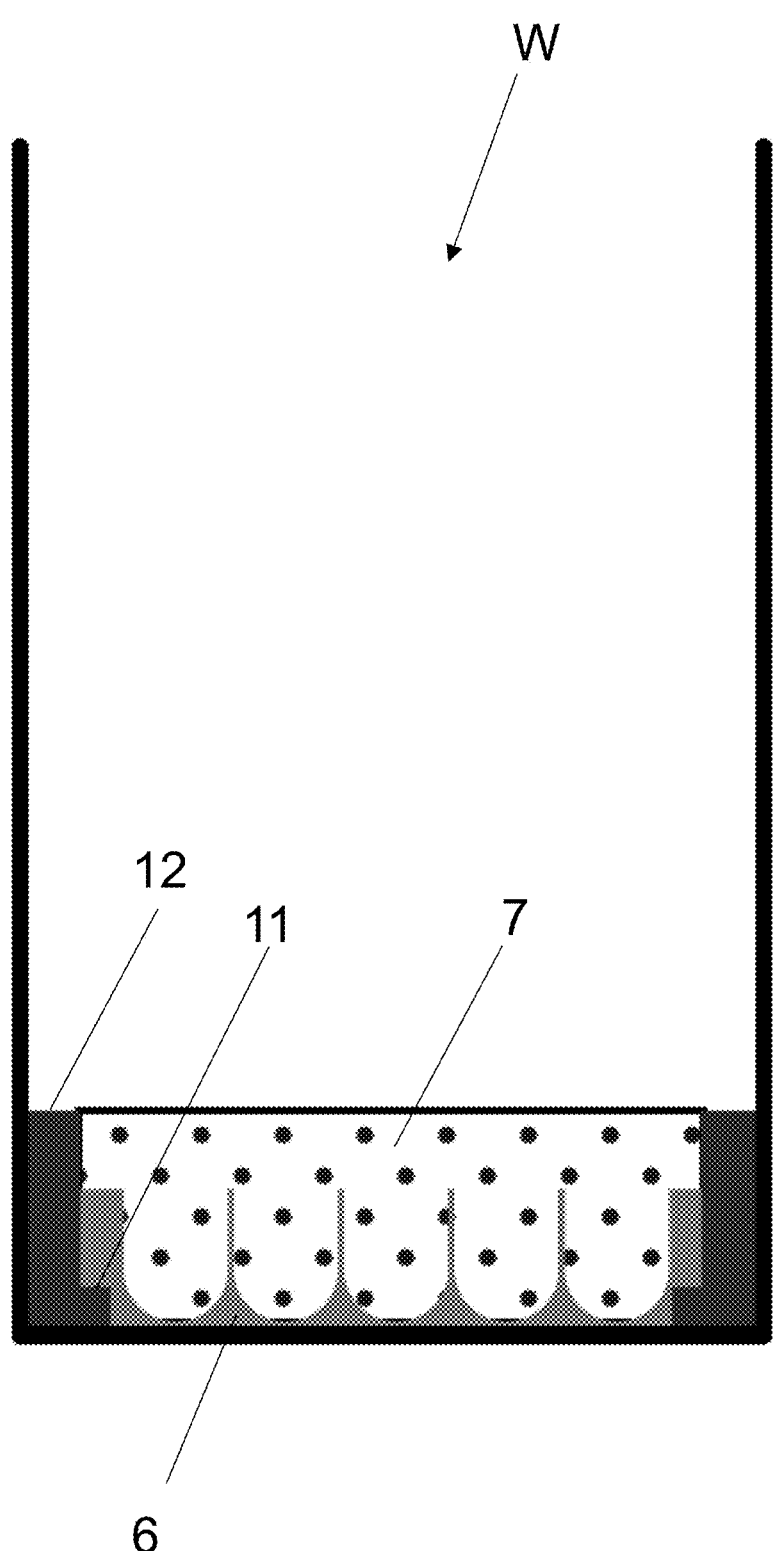
FIG. 7: A schematic visualization of another embodiment of a well according to the disclosure (sectional view)

FIG. 7 shows a schematic visualization of another embodiment of a well W according to the disclosure, yet again in a longitudinal cut view. The well W corresponds to the well W shown in FIG. 6, the sole difference being that the well W in FIG. 7 comprises a microwell-structure 6 which has been molded into the hydrogel drop. Due to the presence of the first internal edge 11, the microwell structure is perfectly homogenous and does not show any malformations. Due to the presence of the second internal edge 12, the culture medium 7 does not form a meniscus with the vertical side wall of the well W. It can be observed that the culture medium does furthermore not develop a pronounced dome (like for example the hydrogel drop 2 in FIG. 6 does). This is simply due to the precise volume of culture medium 7 injected into the well.

Figure 8:
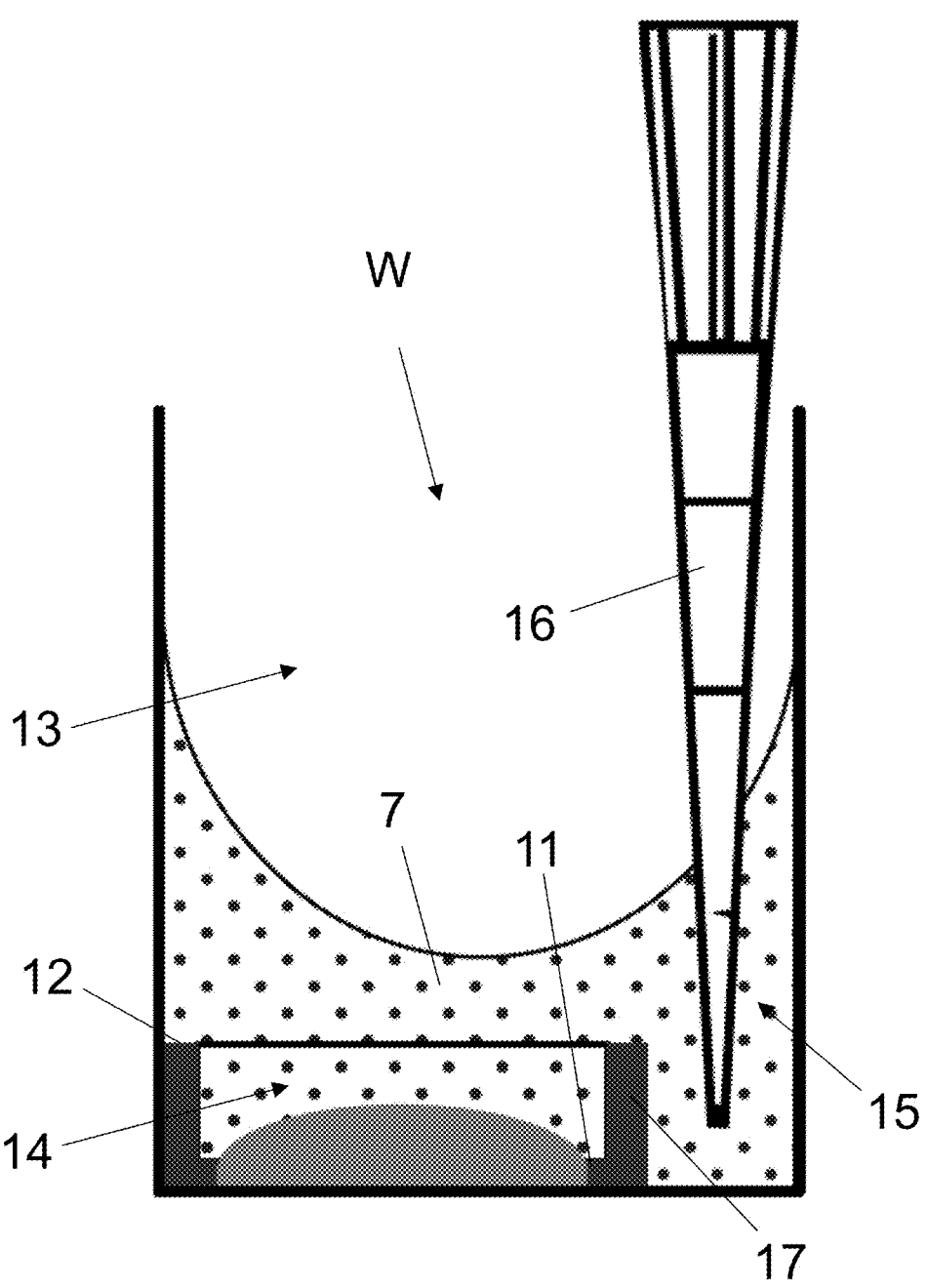
FIG. 8: A schematic visualization of another embodiment of a well according to the disclosure (sectional view)

FIG. 8 shows a schematic visualization of another embodiment of a well W according to the disclosure, yet again in a longitudinal cut view. The well W corresponds to the well W shown in FIG. 6, the sole differences being that the well W in FIG. 8 comprises a pipetting notch 15 and that the culture medium 7 has been topped up by means of a pipette 16. The pipetting notch 15 itself has essentially the form of a round cylinder and is located eccentrically compared to a shared longitudinal axis of the upper cylinder 13 and the bottom area 14. In other words, the pipetting notch 15 is an elongated hole which runs parallel to the upper cylinder 13 and the bottom area 14. The first internal edge 11 together with the second internal edge 12 forms a barrier wall 17 which separates the pipetting notch 15 (in particular a bottom portion of the pipetting notch 15) from the bottom area 14 of the well W. However, no separation is present between the upper cylinder 13 and the pipetting notch 15. The upper cylinder 13 overlaps with the pipetting notch 15, but the bottom area 14 does not overlap with the pipetting notch 15. With this arrangement, the culture medium 7 in the well W can be topped up by inserting a pipette 16 into the pipetting notch 15 and by injecting additional culture medium 7 into the bottom portion of the pipetting notch 15 (as shown in FIG. 7). Like this, an initial amount of culture medium 7, which is already present in the bottom area 14 (see FIG. 6) can easily be topped up while limiting turbulences in the bottom area 14. Instead of being dropped directly onto bottom area 14, the additional culture medium 7 first raises in the bottom portion of the pipetting notch, eventually spills over the barrier wall 17 and then raises up inside the upper cylinder until a desired filling height. Like this, an impact on the culture medium 7 already present in the bottom area 14 is minimized.

Figure 9:
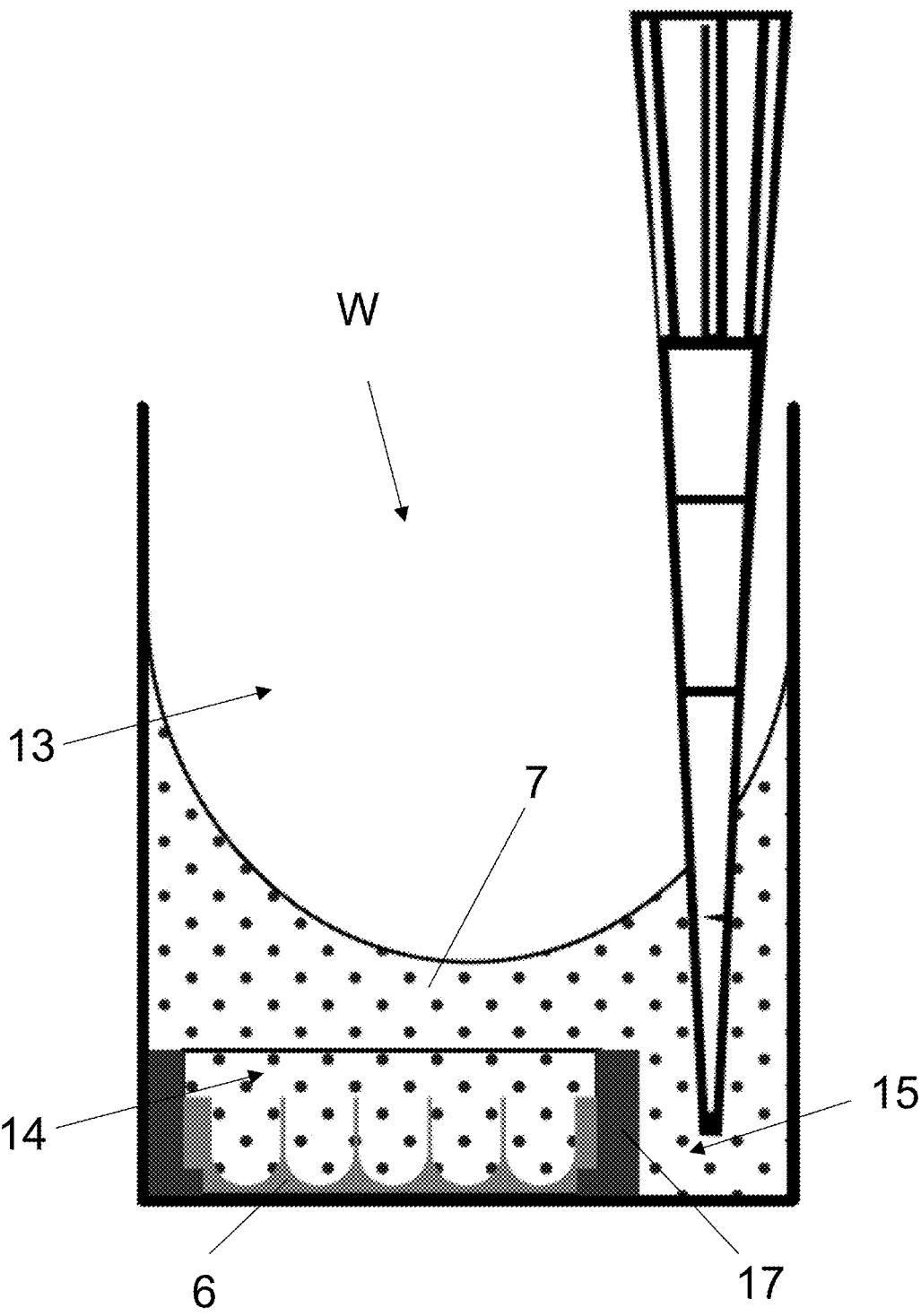
FIG. 9: A schematic visualization of another embodiment of a well according to the disclosure (sectional view)

FIG. 9 shows a schematic visualization of another embodiment of a well W according to the disclosure, yet again in a longitudinal cut view. The well W corresponds to the well W shown in FIG. 8, the sole difference being that the well W in FIG. 9 comprises a microwell-structure 6 which has been molded into the hydrogel drop. In other words: the embodiment shown in FIG. 9 corresponds to the embodiment shown in FIG. 7, but with a pipetting notch 15. Yet again, the barrier wall 17 formed by the two ring-shaped internal edges separates the pipetting notch 15 from the internal area 14, but there is no barriers between the pipetting notch 15 and the upper cylinder 13.

Figure 10:
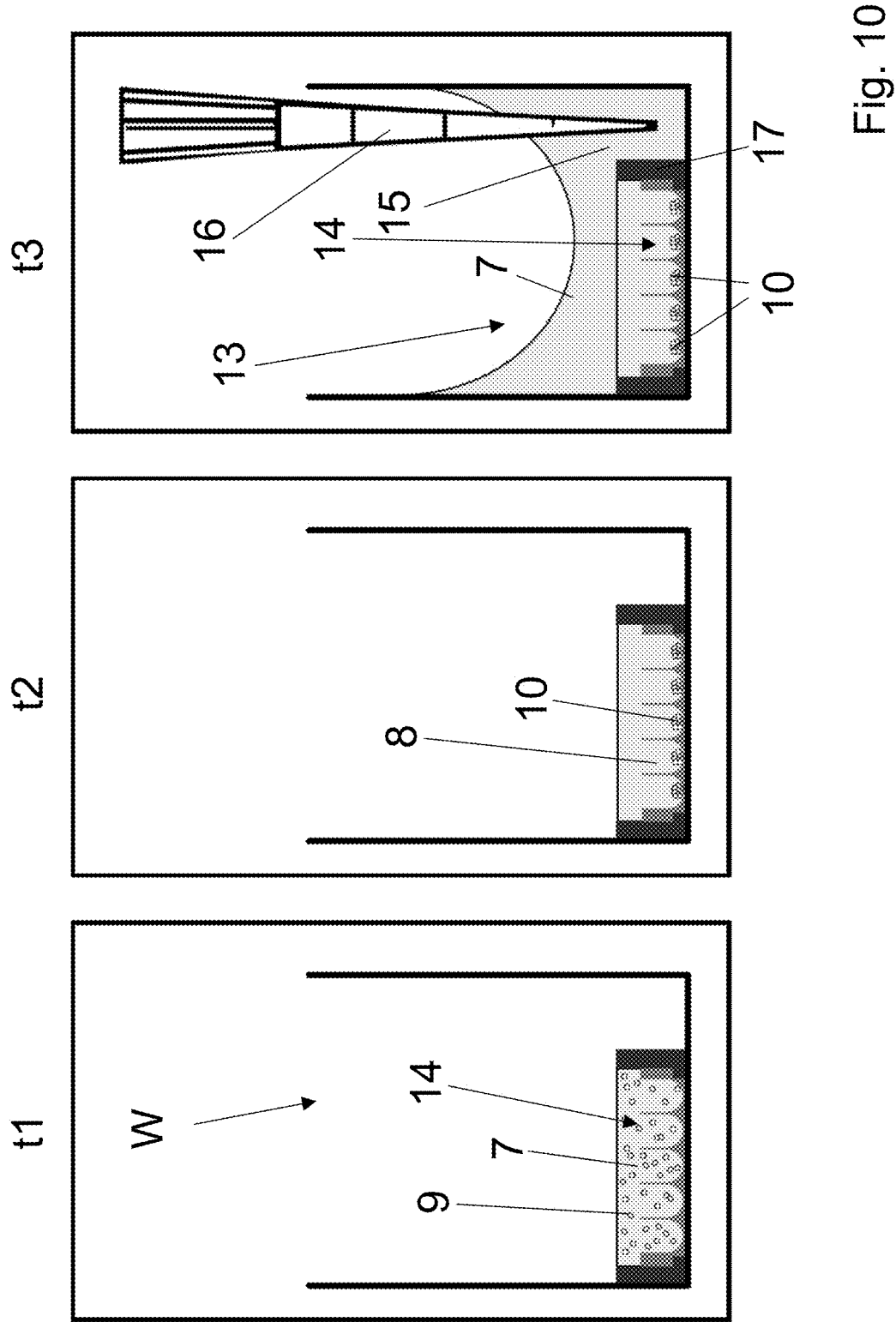
FIG. 10: A schematic visualization of one possible use of the disclosure (sectional view)

FIG. 10 is a schematic visualization of one possible use of the disclosure. Yet again, longitudinal vertical cut through a well W according to one embodiment of the disclosure is shown. The well W shown in FIG. 10 corresponds to the well W shown in FIG. 9, namely a well W comprising a microwell-structure and a pipetting notch. The well W in FIG. 10 is shown at three different moments in time, namely t1, t2 and t3. At moment t1, only the bottom area 14 is filled with a culture medium 7. Moment t1 is just after the culture medium 7 containing cells has been injected into the bottom area 14: This is visualized by little dots representing cells 9 floating around in the culture medium 7. At moment t2, the cells 9 have sedimented into the different microwells 8 and have formed cell colonies 10 of normal size. In particular, due to the fact that the culture medium 7 has not developed a concave meniscus at the side wall of the well W, no too large cell colonies and no too small cell colonies occur (contrarily to the problem of the prior art visualized in FIG. 4). At moment t3, the culture medium 7 has been topped up by means of pipette tip 16 through the pipetting notch 15 as previously explained. Due to the barrier wall 17 which separates the bottom portion of the pipetting notch 15 from the bottom area 14 of the well W, the topping-up has had no strong negative impact on the bottom area 14, and in particular the cell colonies 10 have not been significantly disturbed. Sufficient culture medium 7 is now present in the well W, namely in the bottom area 14 as well as in parts of the upper cylinder 13 and in parts of the pipetting notch 15.

Figure 11:
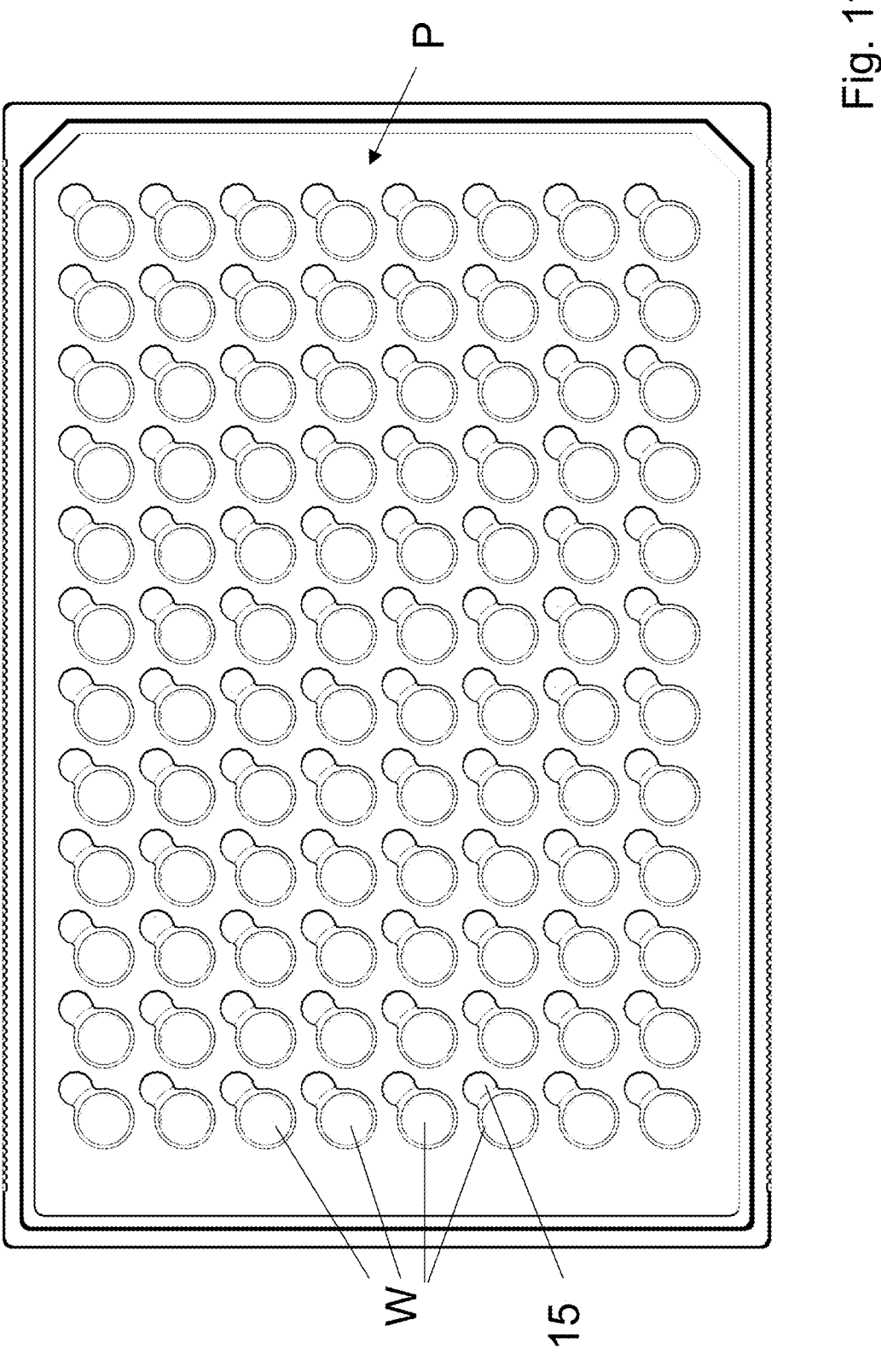
FIG. 11: A schematic visualization of a multi-well plate according to the disclosure (top view)

FIG. 11 shows a schematic visualization of a multi-well plate P according to the disclosure in a top view. The multi-well plate P comprises 96 wells W arranged in eight lines and twelve columns. It can furthermore be seen in FIG. 10 that every well W comprises an eccentric pipetting notch 15. The pipetting notches 15 are arranged at 45 degrees compared to the horizontal direction of FIG. 11. In other words: when holding the multi-well plate P horizontally (that is, with eight lines and twelve columns, such that the twelve wells W of each line align horizontally), then each particular pipetting notch 15 is arranged such that a line which intersects with the vertical axis of the pipetting notch 15 and which also intersects with the vertical axis of the particular well W to which belongs the particular pipetting notch 15 encloses an angle of 45 degrees with the horizontal direction of the multi-well plate P. This particular arrangement leads to a space optimization on the multi-well plate P. Other possibilities are angles of 135, 225 or 315 degrees.

Figure 12:
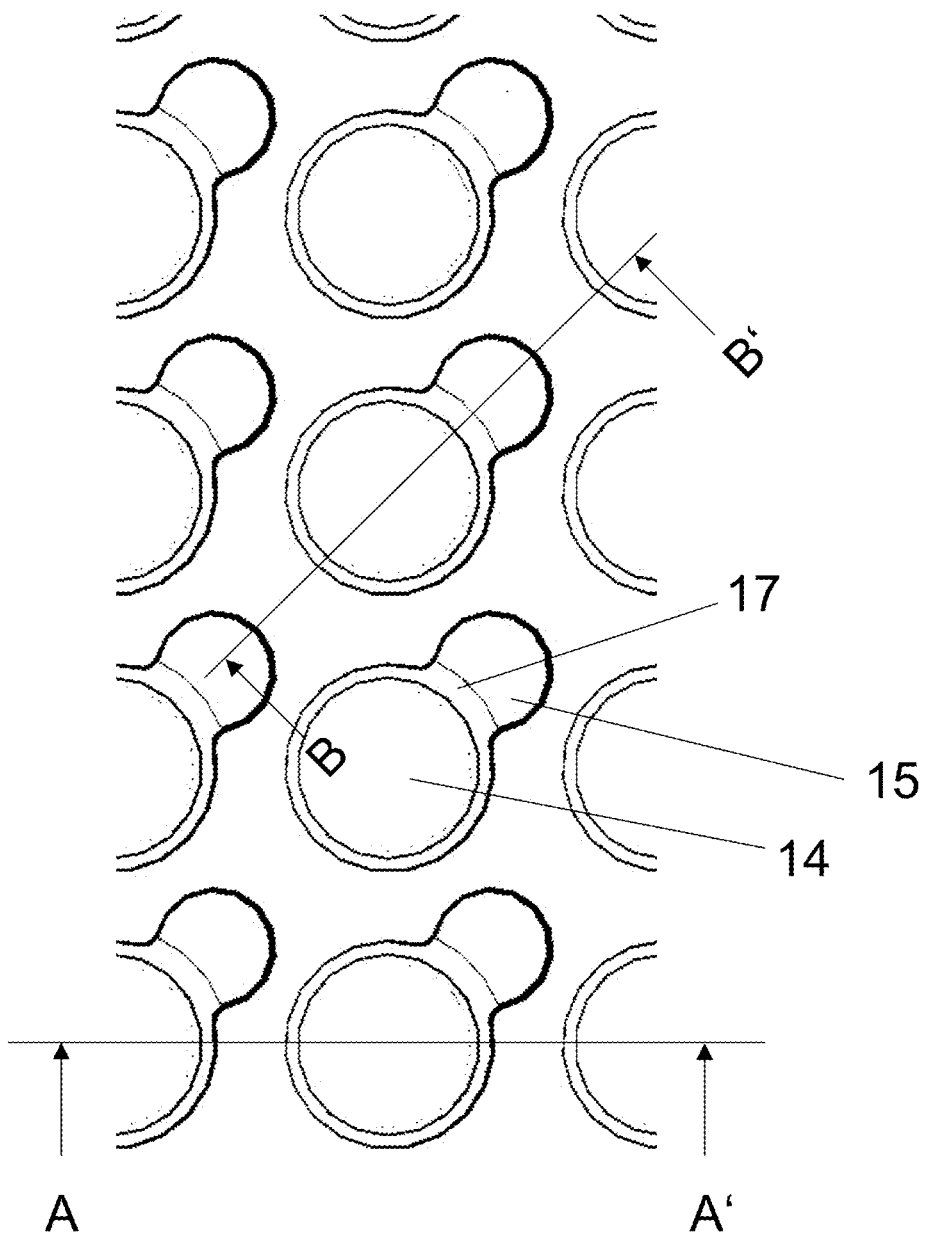
FIG. 12: A zoom-in on the multi-well plate of FIG. 11, in which cutting lines are indicated.

FIG. 12 shows a zoom-in on the multi-well plate of FIG. 11, in which cutting lines are indicated. In particular, FIG. 12 shows a cutting line A-A' which passes through the centers of three wells W without running through the pipetting notches and a cutting line B-B' which passes through the centers of three wells W while also running through the centers of the pipetting notches 15. FIG. 12 also clearly shows the barrier walls 17 which separate the bottom area 14 of each well from the pipetting notch 15.

Figure 13:
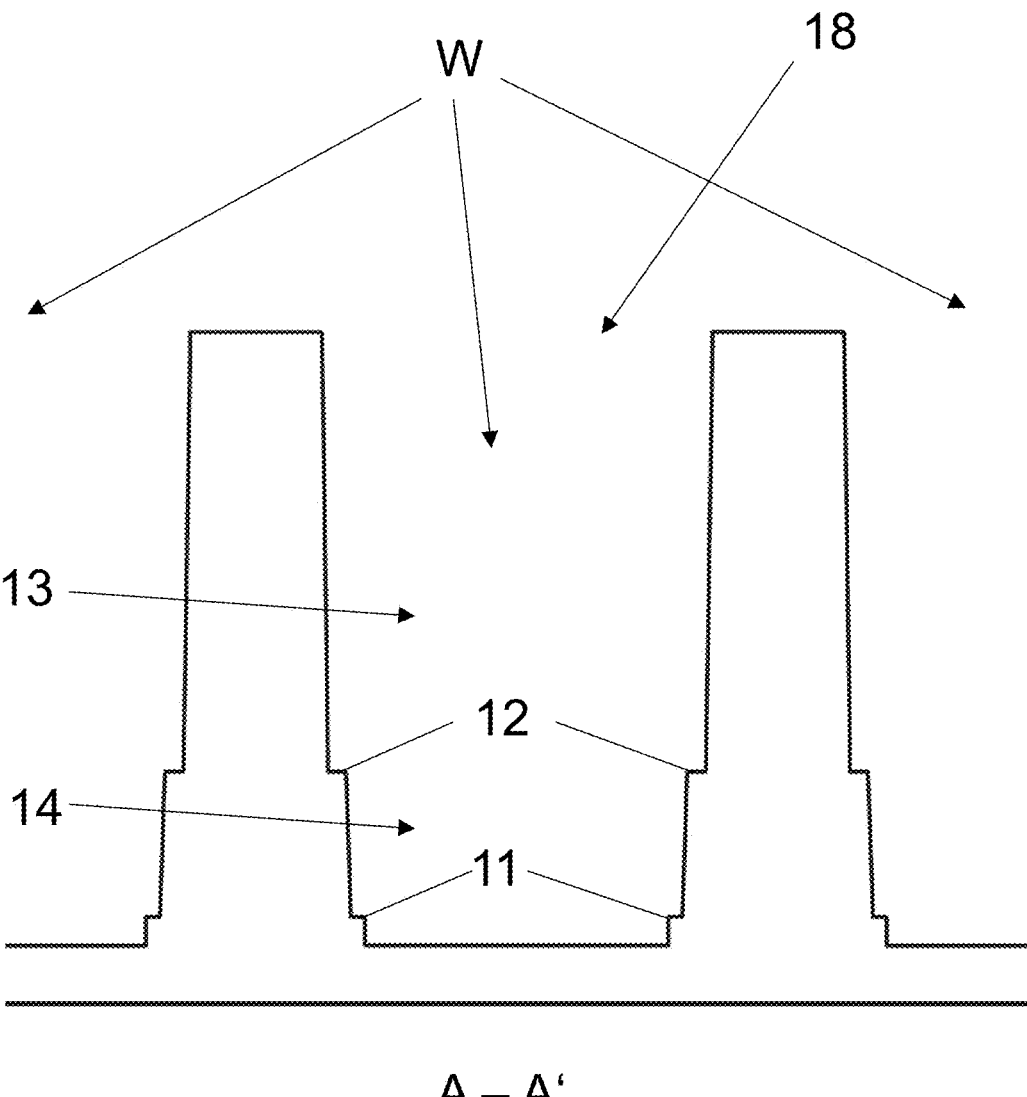
FIG. 13: A sectional view according to the cutting line A-A indicated in FIG. 12, FIG. 14: A sectional view according to the cutting line B-B' indicated in FIG. 12, FIG. 15: Another partial sectional view through the multi-well plate shown in FIG. 12 (CAD-rendered view)

FIG. 13 shows a sectional view according to the cutting line A-A indicated in FIG. 12. Three wells W are perceivable, wherein only the well W in the middle is fully shown. The well W on the right and the well W on the left are only partly shown. The well W in the middle (just like all wells W) comprises a top opening 18, as well as a first internal edge 11 and a second internal edge 12. The internal edges 11, 12 are both ring-shaped with a common vertical axis. The internal edges 11, 12 are comprised in the bottom area 14. The bottom area 14 extends from a bottom of the well W upwards to the upper end of the second internal edge 12. Indicated by reference sign in FIG. 13 is also an upper cylinder 13 which extends upwards from the upper end of the second internal edge 12, towards the top opening 18. The side wall of the upper cylinder 13 as well as the inner wall of the ring-shaped second internal edge 12 are not completely vertical, but inclined by a few degrees. They are referred to as being essentially vertical or near vertical. Furthermore, the bottom area 14 as well as the upper cylinder 13 are referred to as being essentially hollow cylindrical, even if at least some of their side walls are lightly inclined and even if the ring-shaped internal edged 11, 12 lead to modifications of the internal diameter of these parts of the well.

Figure 14:
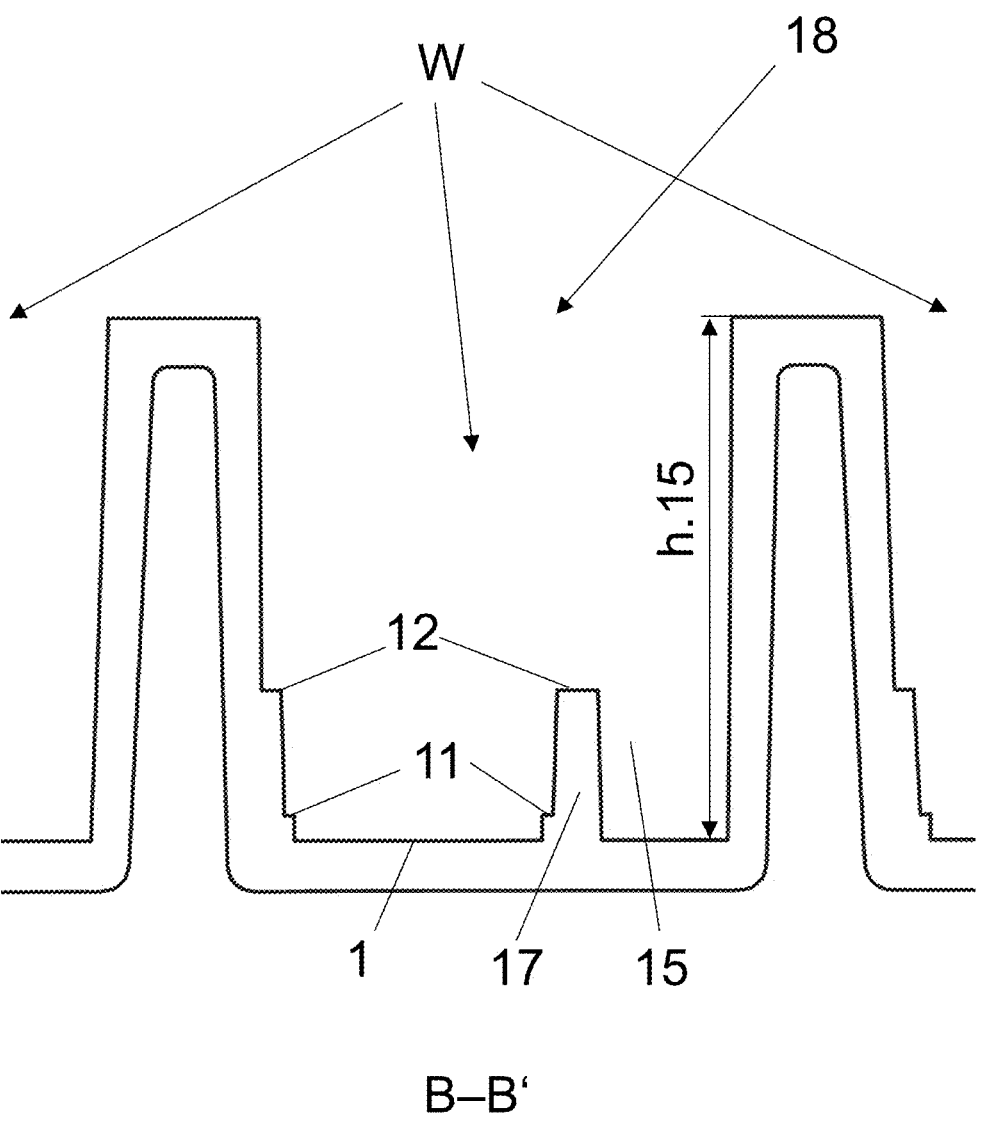

FIG. 14 shows a sectional view according to the cutting line B-B' indicated in FIG. 12. The multi-well plate P on which the sectional view B-B' is based is not necessarily the same as the multi-well plate on which the cut A-A' in FIG. 13 is based. Yet again, also in FIG. 14, many features already shown in FIG. 13 are perceivable, for example three wells W are perceivable, wherein only the well W in the middle is fully shown. The well W on the right and the well W on the left are only partly shown. The well W in the middle (just like all wells W) comprises a top opening 18, as well as a first internal edge 11 and a second internal edge 12. The internal edges 11, 12 are both ring-shaped with a common vertical axis. Furthermore, the pipetting notch 15 is also perceivable in FIG. 15 and has a height h.15 which corresponds to the overall depth of the well, i.e. the distance between the top opening 18 and the flat bottom 1 of the well. Furthermore the barrier wall 17 formed by parts of the internal edges 11, 12 is also shown in FIG. 14.

Figure 15:
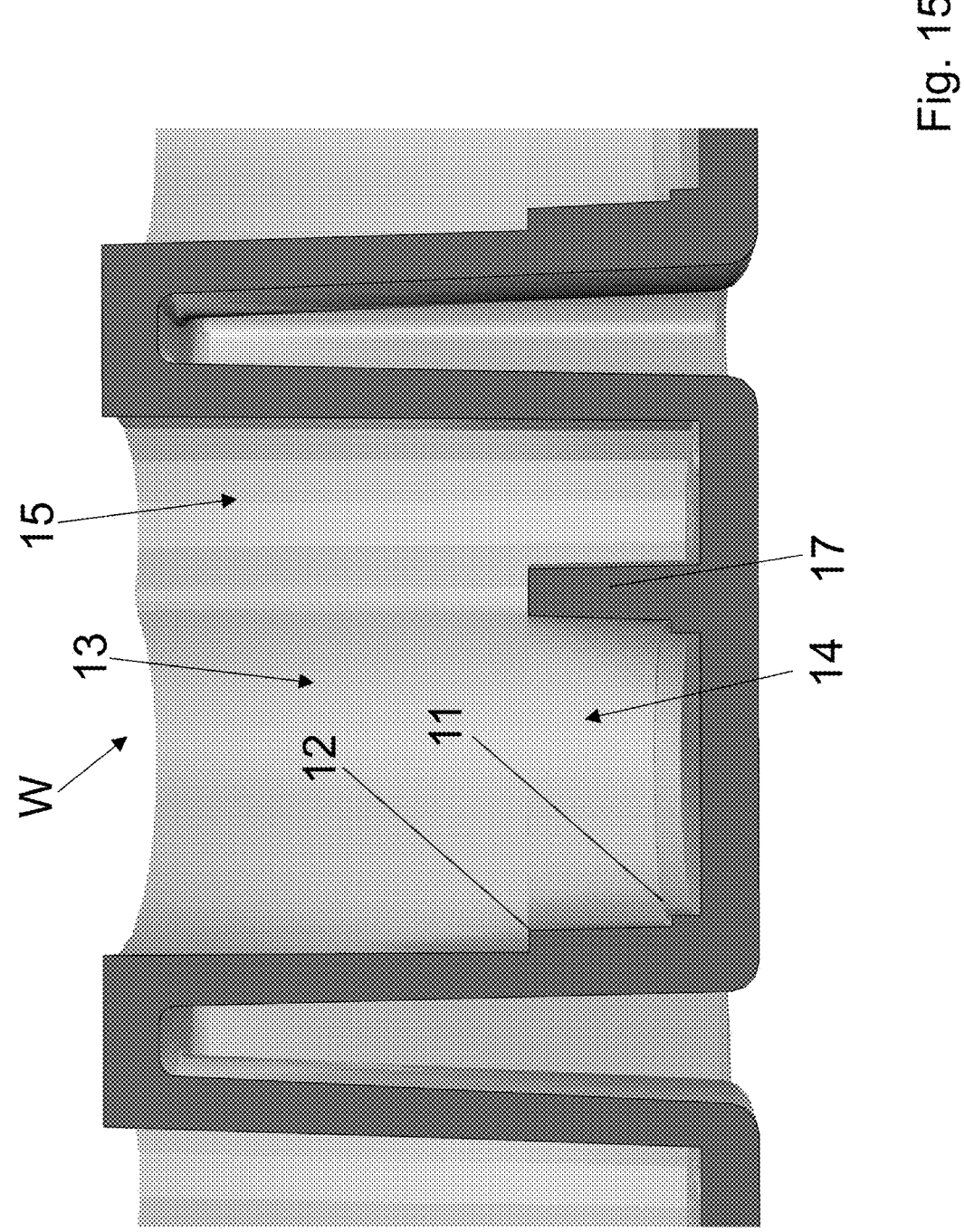

FIG. 15 shows another partial sectional view through a multi-well plate P like the one shown in FIG. 12, namely a CAD-rendered view. In particular, FIG. 15 shows a well W comprising an upper cylinder 13, a bottom area 14 and a pipetting notch 15. FIG. 15 clearly shows that the barrier wall 17 forms a separation between the bottom area 14 and the pipetting notch 15, in particular a bottom portion of the pipetting notch 15, whereas no barrier is present between the upper cylinder 13 and the pipetting notch 15, in particular an upper portion of the pipetting notch 15. It is also perceivable in FIG. 15 that both internal edges 11, 12 are circumferential rings running around in circles around the inner wall of the bottom area 14 of the well, wherein the second internal edge 12 is arranged on top of the first internal edge 11, and wherein the edges 11, 12 form the barrier wall 17.

Figure 16:
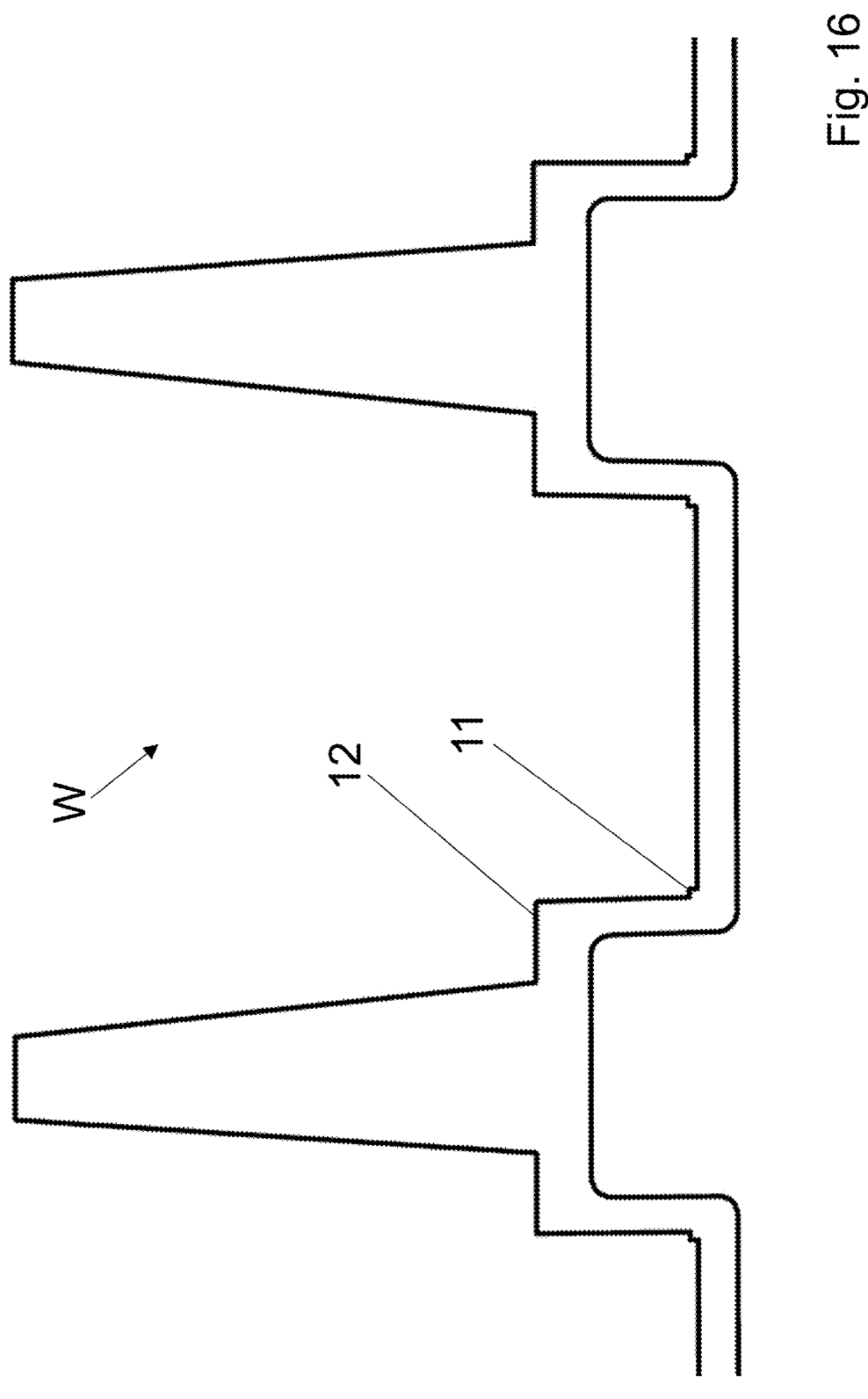
FIG. 16: A partial sectional view through a multi-well plate according to another embodiment of the disclosure.

FIG. 16 shows a partial sectional view through a multi-well plate P according to another embodiment of the disclosure. Also in this embodiment, the well W comprises a first internal edge 11 and a second internal edge 12. The internal edges 11, 12 in FIG. 16 are comparable to the internal edges 11, 12 shown in the previous figures, even if their dimensions are—as can easily be observed—different. This visualizes that different dimensions of the internal edges 11, 12 are possible when implementing the disclosure.

Figure 17:
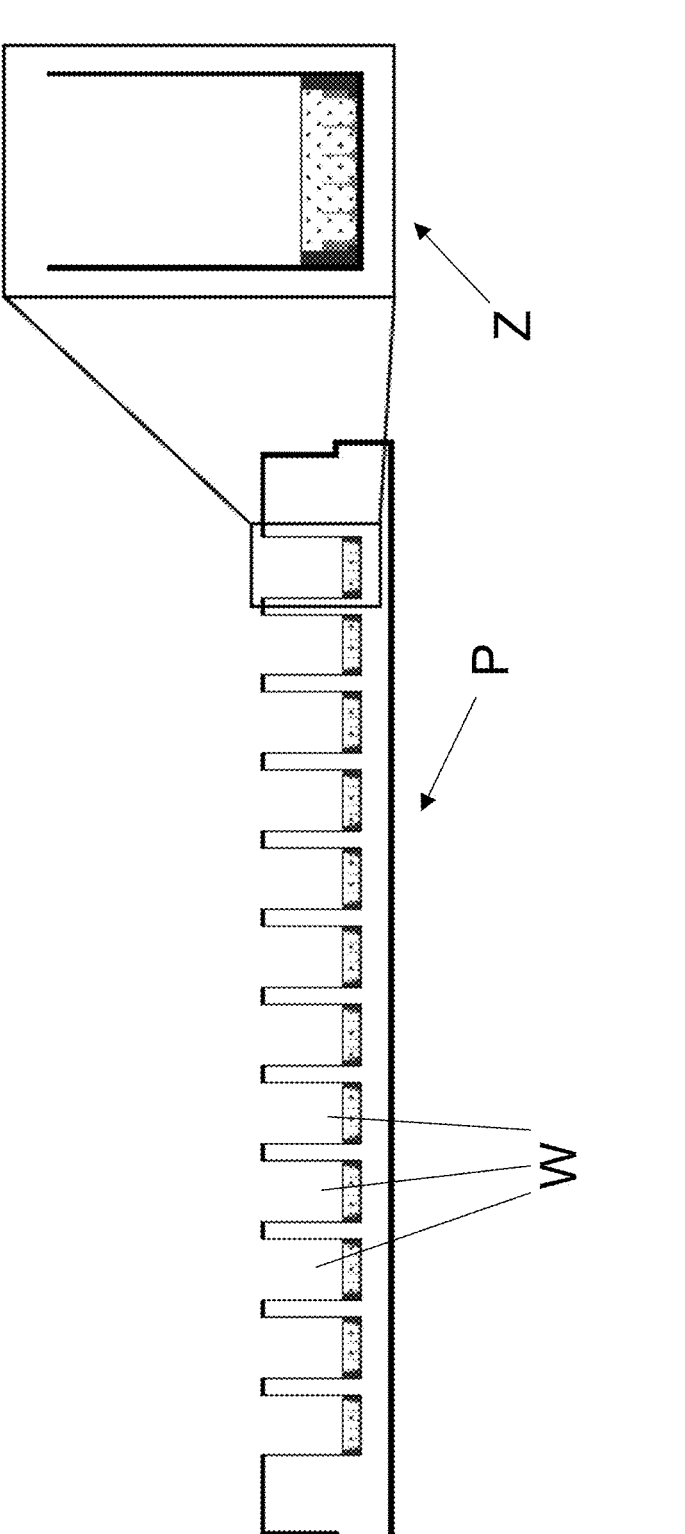
FIG. 17: A schematic visualization of a multi-well plate according to the disclosure (sectional view with zoom-in on one well, FIG. 18: A schematic visualization of other embodiments of a well according to the disclosure (sectional view), FIG. 19: A schematic visualization of another embodiment of a well according to the disclosure (sectional view), FIG. 20: A schematic visualization of the longitudinal axes of the well, the upper cylinder, the bottom area and the pipetting notch (sectional view).

FIG. 17 shows a schematic visualization of a multi-well plate P according to the disclosure, namely a sectional view (vertical cut) of a multi-well plate P with a zoom-in Z on one well W. Twelve identical wells W are shown cut along their entire depth in the multi-well plate P. The wells W in FIG. 17 correspond to the wells shown in FIG. 7.

Figure 18:
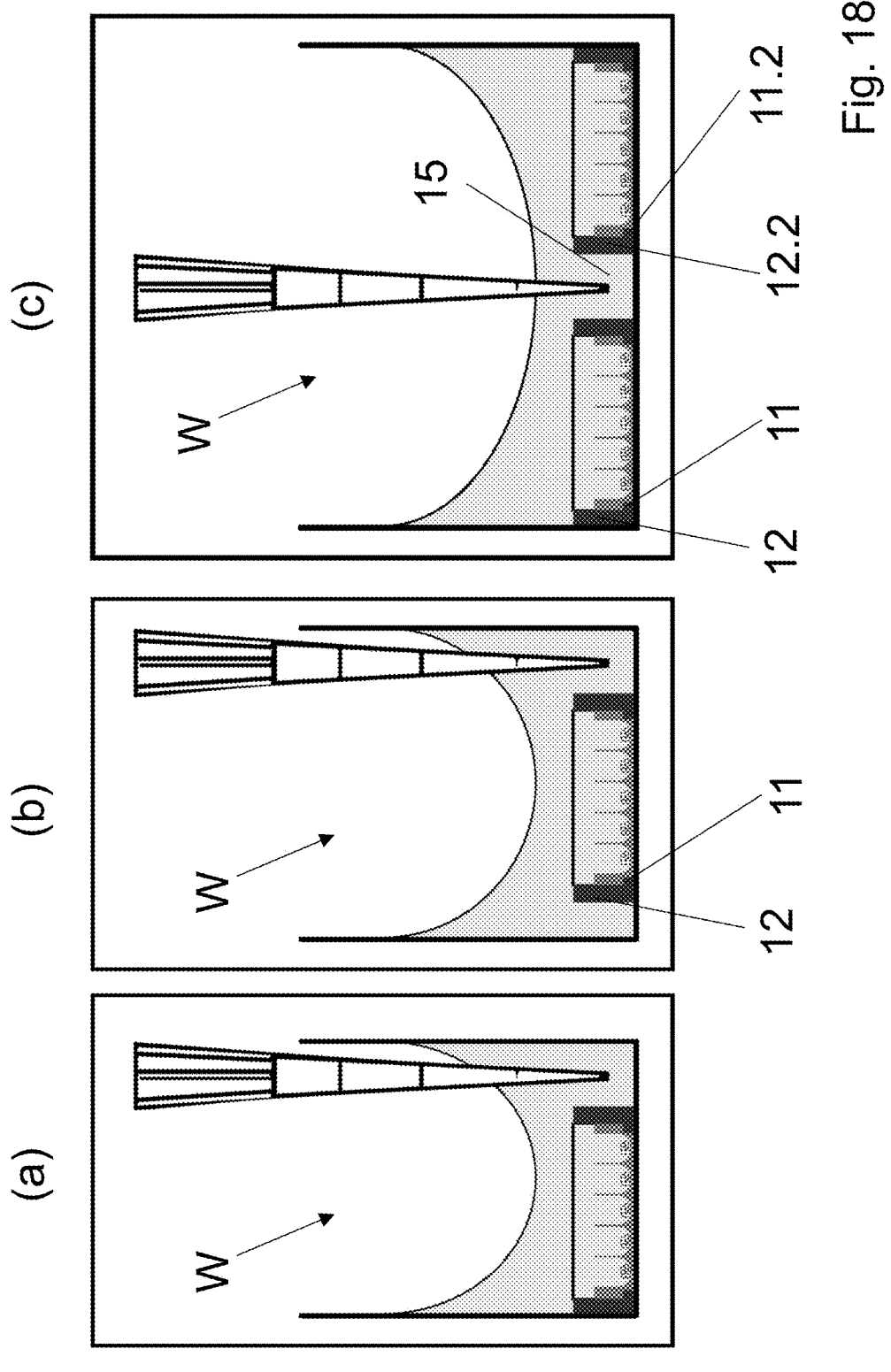

FIG. 18 shows schematic visualization of other embodiments of a well W according to the disclosure (sectional view). In image (a) of FIG. 18, a well W according to the well already shown in FIG. 10 is depicted. The well W in image (b) is in principle comparable to the well W shown in image (a), but the first internal edge (11) and the second internal edge (12) of the well W shown in image (b) of FIG. 18 are not attached to the wall of the well W but are free-standing rings attached to the bottom of well W. In image (c) of FIG. 18, yet another embodiment of a well W is shown: in addition to the first internal edge (11) and the second internal edge (12), the well W comprises a supplementary first internal edge (11.2) and a supplementary second internal edge (12.2). All if these internal edges (11, 11.2, 12, 12.2) are rings attached to the bottom of the well W but are not circumferential running around the vertical side wall of well W depicted in image (c) of FIG. 18. These rings can be described as partly free-standing because they are only partly attached to the side wall of the well W. From image (c) it becomes clear that a well W with a sufficiently large diameter can in principle comprise a multitude of first internal edges and a multitude of second internal edges.

Figure 19:
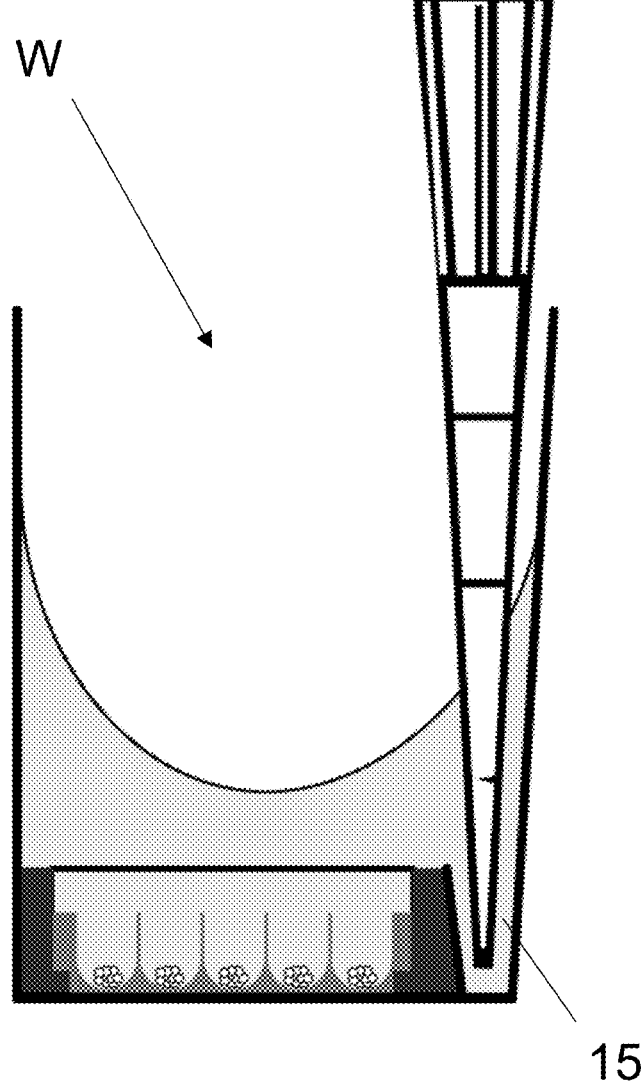

FIG. 19 shows a schematic visualization of another embodiment of a well W according to the disclosure, yet again in a vertical cut view running through its longitudinal axis. The well W in principle corresponds to the well W depicted in image (a) of FIG. 18, but the pipetting notch 15 is of the well W in FIG. 19 is conical. In particular, the conical pipetting notch 15 becomes gradually narrower towards the bottom of the well W.

Figure 20:
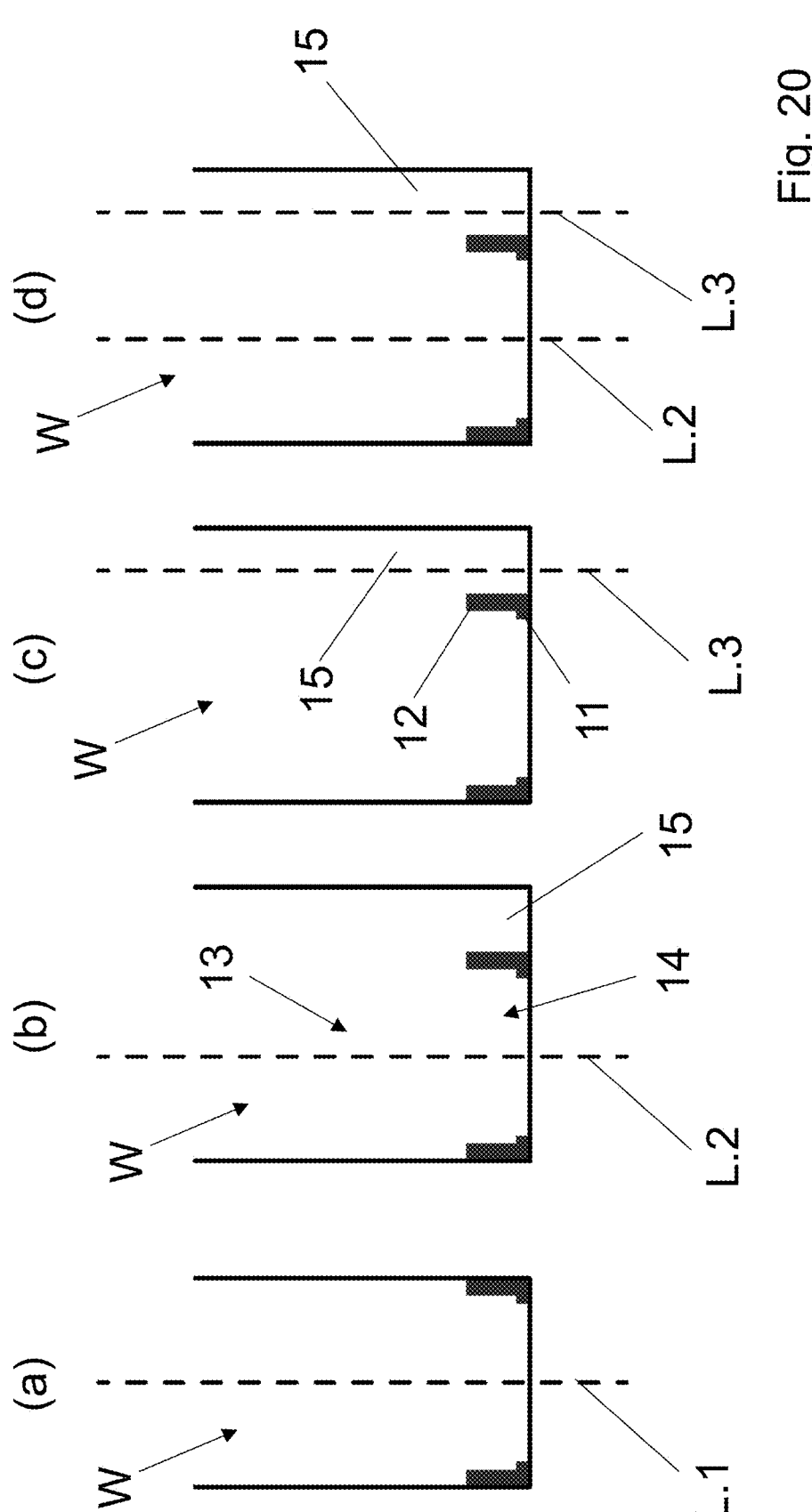

FIG. 20 shows a schematic visualization of the longitudinal axes of the well, the upper cylinder, the bottom area and the pipetting notch (sectional view). In particular, image (a) of FIG. 20 shows a well W which has the form of a cylinder. The well W has a longitudinal axis L.1 running in vertical direction through the center of the bottom of the well W and through the center of the top opening of the well W. Image (b) of FIG. 20 shows a well W with pipetting notch 15. The upper cylinder 13 and the bottom area 14 of the well W share a common longitudinal axis L.2, but this longitudinal axis L.2 is not necessarily the longitudinal axis of the well W because the well W now has a complex horizontal section instead of a simple round horizontal section due to the presence of the pipetting notch 15. This complex form of the well W with pipetting notch 15 can be observed in the top views shown in FIGS. 11 and 12. The wells W in images (c) and (d) of FIG. 20 correspond to the well W in image (b) of FIG. 20. However, in image (c) is indicated the longitudinal axis L.3 of the pipetting notch 15. When one looks at the bottom portion of the pipetting notch 15, one realizes that the longitudinal axis L.3 appears to not exactly run through the center of the free bottom surface of the pipetting notch 15. The reason for this is that the first internal edge 11 and the first internal edge 12 actually protrude into the pipetting notch 15. In other words; the pipetting notch 15 overlaps with the rest of the well W and vise-versa. In image (d) of FIG. 20, the horizontal axis L.3 of the pipetting notch 15 as well as the common longitudinal axis L.2 of the upper cylinder 13 and the bottom area 14 are both indicated for the purpose of further clarification. A distance between the two longitudinal axes L.2 and L.3 is smaller than the sum of the radius of the pipetting notch 15 and the radius of the upper cylinder 13 and/or the external radius of the bottom area 14.

The invention is not limited to the preferred embodiments described here. The scope of protection is defined by the claims.

Furthermore, the following claims are hereby incorporated into the Detailed Description, where each claim may stand on its own as a separate embodiment. While each claim may stand on its own as a separate embodiment, it is to be noted that—although a dependent claim may refer in the claims to a specific combination with one or more other claims—other embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

In general, throughout the description and the claims, the terms "preferably", "preferred" and the like shall be interpreted as relating to preferred features, which do, however, not necessarily have to be put in place. Likewise, the terms "typically", "typical" and the like shall be interpreted as relating to preferred features and/or advantageous features and/or typical features, which do, however, not necessarily have to be put in place.

It is further to be noted that methods disclosed in the specification or in the claims may be implemented by a device having means for performing each of the respective acts of these methods.

All the features and advantages, including structural details, spatial arrangements and method steps, which follow from the claims, the description and the drawing can be fundamental to the invention both on their own and in different combinations. It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

REFERENCE LIST

1 Flat bottom (of well)
2 Hydrogel drop (typically forming a convex meniscus)
3 (Near) Vertical side wall (of well)
4 Concave meniscus
5 Stamp
6 Microwell-structure
6.1 Malformed microwell-structure
7 Culture medium
8 Microwell
9 Cells
10 Cell colonies (normal size)
10.1 Cell colonies (too large)
10.2 Cell colonies (too small)
11 First internal edge
12 Second internal edge
13 Upper cylinder
14 Bottom area
15 Pipetting notch
16 Pipette tip
17 Barrier wall
18 Top opening (of well)
W Well
P Multi-well plate
Z Zoom-in
L.1, L.2, L.3 Longitudinal axes
h.13 Height of upper cylinder
h.14 Height of bottom area
h.15 Height of pipetting notch
t1, t2, t3 Moments in time (not necessary always the same)
A-A' Vertical cut through multi-well plate (cut not running through pipetting notch)
B-B' Vertical cut through multi-well plate (cut running through pipetting notch)

The invention claimed is:

1. A multi-well plate comprising a plurality of wells for cultivating biological material, each well of the plurality of wells comprising:
a vertical side wall;
a top opening;
a bottom area comprising a first internal edge;
a second internal edge arranged on top of the first internal edge;
an upper cylinder extending from the top opening to the second internal edge;
a cylindrical pipetting notch; and
a barrier wall, formed by the first internal edge and the second internal edge, located between the pipetting notch and the bottom area,
wherein the bottom area extends from the second internal edge to a bottom of the well,
wherein the first and second internal edge are annular with a rectangular section and are partially circumferential along a longitudinal axis of the well,
wherein the second internal edge is arranged on top of the first internal edge on a side of the first internal edge, which is opposite to the side with which the first internal edge sits on the bottom of the well,
wherein the second internal edge has a larger internal diameter than the first internal edge and is higher than the first internal edge,

wherein the first and second internal edges form the barrier wall,
wherein the second internal edge does not form the vertical side wall of the well thereby the second internal edge has larger internal diameter than the vertical side wall and/or is a length apart along the horizontal axis from the vertical side wall,
wherein each well of the plurality of wells comprises a microwell-structure, the microwell-structure comprising a plurality of microwells, and
wherein the microwell-structure is made of stamped hydrogel in the bottom area of the well.

2. The multi-well plate according to claim 1, wherein each well of the plurality of wells is configured to receive the stamped hydrogel as a hydrogel drop in the bottom area, wherein the first internal edge is configured to force the hydrogel drop to develop a dome surface after a sufficient volume of the hydrogel drop has been placed in the bottom area of the well.

3. The multi-well plate according to claim 1, wherein at least a part of the first internal edge and/or the second internal edge is essentially circumferential and/or essentially ring-like.

4. The multi-well plate according to claim 3, wherein the first internal edge is located between a bottom of the well and the second internal edge.

5. The multi-well plate according to claim 3, wherein at least a part of each well of the plurality of wells is essentially cylindrical, wherein at least a part of the upper cylinder and/or the bottom area is essentially cylindrical with an essentially round section.

6. The multi-well plate according to claim 5, wherein an internal diameter of the bottom area is smaller than an internal diameter of the upper cylinder.

7. The multi-well plate according to claim 5, wherein the upper cylinder and the bottom area and the first internal edge are molded into one and the same workpiece, wherein the second internal edge is also molded into the same workpiece, wherein the workpiece is made from plastic and/or wherein a wall thickness of the workpiece is essentially constant throughout the entire well.

8. The multi-well plate according to claim 5, wherein the pipetting notch is essentially circular cylindrical, wherein a longitudinal axis (L.3) of the pipetting notch and a longitudinal axis (L.2) of the upper cylinder are parallel, wherein a distance between the longitudinal axis (L.3) of the pipetting notch and the longitudinal axis (L.2) of the upper cylinder is smaller than a sum of an inner radius of the upper cylinder and an inner radius of the pipetting notch, such that the upper cylinder and the pipetting notch overlap, at least along a fraction of the depth of the well, such that an opening is present between the pipetting notch and the upper cylinder.

9. The multi-well plate according to claim 8, wherein a height of the pipetting notch equals the sum of a height of the upper cylinder and a height of the bottom area, wherein a height (h.15) of the barrier wall equals the height (h.14) of the bottom area.

10. The multi-well plate according to claim 8, wherein the multi-well plate comprises a main body, wherein the wells and/or all hollow cylinders and/or all internal edges and/or all pipetting notches are molded into the main body, wherein a wall thickness of the main body is essentially constant throughout the main body.

11. A method for manufacturing the multi-well plate according to claim 10, comprising:

forming a main body comprising the multitude of the wells, wherein the main body is formed by means of injection molding, injecting a hydrogel drop into the bottom area of each well, and stamping a microwell-structure into each hydrogel drop.

12. The multi-well plate according to claim 1, wherein each well of the plurality of wells comprises a first hollow cylinder, wherein the first hollow cylinder comprises a first top rim, wherein at least a part of the first top rim forms the first internal edge, wherein the first hollow cylinder extends from a bottom of the well towards the top opening, wherein the first hollow cylinder is placed concentrically inside the bottom area wherein an external diameter of the first hollow cylinder equals the internal diameter of the bottom area.

13. The multi-well plate according to claim 12, wherein each well of the plurality of wells comprises a second hollow cylinder, wherein the second hollow cylinder comprises a second top rim, wherein at least a part of the second top rim forms the second internal edge.

* * * * *